US012781155B2

(12) United States Patent
Bauer et al.

(10) Patent No.: US 12,781,155 B2
(45) **Date of Patent: *Nov. 3, 2026**

(54) MIXED HYDROXYETHER COMPOUNDS, PROCESS FOR MAKING SUCH COMPOUNDS, AND THEIR USE

(71) Applicant: BASF SE, Ludwigshafen am Rhein (DE)

(72) Inventors: Frederic Bauer, Ludwigshafen (DE); Heike Weber, Ludwigshafen (DE); Andreas Schwallenberg, Düsseldorf-Holthausen (DE); Peter Klotz, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 668 days.

This patent is subject to a terminal disclaimer.

(21) Appl. No.: 17/996,128

(22) PCT Filed: Mar. 22, 2021

(86) PCT No.: PCT/EP2021/057301
§ 371 (c)(1),
(2) Date: Oct. 13, 2022

(87) PCT Pub. No.: WO2021/089887
PCT Pub. Date: May 14, 2021

(65) Prior Publication Data

US 2023/0203400 A1 Jun. 29, 2023

(30) Foreign Application Priority Data

Jul. 2, 2020 (EP) .................................... 20183683

(51) Int. Cl.

| | |
|---|---|
| ***C11D 1/72*** | (2006.01) |
| ***C07C 41/03*** | (2006.01) |
| ***C07C 43/10*** | (2006.01) |
| ***C07C 43/11*** | (2006.01) |
| ***C08G 65/26*** | (2006.01) |
| ***C11D 3/20*** | (2006.01) |
| ***C11D 3/37*** | (2006.01) |

(52) U.S. Cl.
CPC .............. *C11D 1/721* (2013.01); *C07C 41/03* (2013.01); *C07C 43/10* (2013.01); *C07C 43/11* (2013.01); *C08G 65/2609* (2013.01); *C08G 65/2696* (2013.01); *C11D 3/2068* (2013.01); *C11D 3/3707* (2013.01); *C11D 2111/14* (2024.01)

(58) Field of Classification Search
CPC ... C11D 1/721; C11D 2111/14; C11D 3/3707; C11D 3/2068; C07C 41/03; C07C 43/11; C07C 43/10; C08G 65/2609; C08G 65/2696
See application file for complete search history.

(56) References Cited

U.S. PATENT DOCUMENTS

| | | | | |
|---|---|---|---|---|
| 6,462,006 | B1 | 10/2002 | Sorg et al. | |
| 7,022,662 | B2 * | 4/2006 | Kischkel ................ | C11D 1/721 510/505 |
| 8,303,721 | B2 | 11/2012 | Warkotsch et al. | |
| 2003/0045448 | A1 | 3/2003 | Weuthen et al. | |
| 2004/0063602 | A1 | 4/2004 | Schmid et al. | |

FOREIGN PATENT DOCUMENTS

| | | | |
|---|---|---|---|
| DE | 2432757 | A1 | 1/1976 |
| DE | 19819187 | A1 | 11/1999 |
| EP | 0851023 | A2 | 7/1998 |
| WO | 2008095563 | A1 | 8/2008 |

OTHER PUBLICATIONS

European Search Report for EP Patent Application No. 20183683.0, Issued on Dec. 15, 2020, 3 pages.
International Search Report and Written Opinion for PCT/EP2021/057301 issued on Apr. 23, 2021, 8 pages.

* cited by examiner

*Primary Examiner* — Rabon A Sergent
(74) *Attorney, Agent, or Firm* — Armstrong Teasdale LLP

(57) ABSTRACT

Described herein are compounds according to general formula (I)

$$R^1—CHR^2—CH_2—O-(AO)_x—CH_2—CH(OH)—R^3 \quad (I).$$

wherein
$R^1$ is linear or branched, unsubstituted $C_2$-$C_4$-alkyl,
$R^2$ is linear or branched, unsubstituted alkyl group bearing two carbon atoms more than $R^1$,
x is an integer in a range of from 10 to 35,
AO is identical or different and selected from the group consisting of $CH_2—CH_2—O$, $(CH_2)_3—O$, $(CH_2)_4—O$, $CH_2CH(CH_3)—O$, $CH(CH_3)—CH_2—O—$ and $CH_2CH(n\text{-}C_3H_7)—O$, and
$R^3$ is linear or branched, unsubstituted or substituted $C_6$-$C_{18}$-alkyl.
Also described herein are a process to make the compounds according to general formula (I), and a method of using the compounds according to general formula (I) in a composition for automatic dishwashing.

14 Claims, No Drawings

MIXED HYDROXYETHER COMPOUNDS, PROCESS FOR MAKING SUCH COMPOUNDS, AND THEIR USE

CROSS-REFERENCE TO RELATED APPLICATIONS

This application is a U.S. National Phase Application of PCT/EP2021/057301, filed Mar. 22, 2021, which claims the benefit of priority to European Patent Application No. 20183683.0, filed Jul. 2, 2020, the entire contents of which are hereby incorporated by reference herein.

FIELD OF INVENTION

The presently claimed invention is directed towards compounds according to general formula (I). The presently claimed invention further relates to a process to make such compounds, and to their use in a composition for automatic dishwashing.

BACKGROUND OF THE INVENTION

Detergent formulations, especially detergent formulations for automatic dishwashing, have to meet various requirements. When being used in automatic dishwashing, such detergent formulations need to enable a complete cleaning of china, polymer, metal, clay, and glassware and to remove all sorts of soil, like fat, proteins, starch, dyes, and more. The soil needs to be dispersed in water during the cleaning and the water removal process, and the various soils should not deposit in the dishwashing machine in case of automatic dishwashing. Finally, during the drying process, the cleaned good should exhibit a good drying behavior, without spotting.

Mixed hydroxy ethers ("HME's") are particularly efficient non-ionic surfactants for rinsing, especially when combined with certain polymers, see, e.g., WO 2008/095563. However, their rinsing performance can still be improved. They should show an overall excellent behavior with respect to spotting and processability, especially in the fields of tablet stability and spraying safety. In addition, an overall high compatibility with materials such as silver, ceramics and polymers used for plastic dishes is highly desired.

It was therefore an objective of the present invention to provide an automatic dishwashing formulation that shows a still improved spotting behavior. In particular, it was an objective to provide ingredients that allow the manufacture of an automatic dishwashing formulation that has improved spotting behavior and high compatibility with a wide variety of materials.

SUMMARY OF THE INVENTION

Surprisingly it was found that the compounds of the present invention improve the spotting behavior when used in dishwashing compositions.

Thus, in one aspect, the presently claimed invention is directed to a compound according to general formula (I)

$$R^1—CHR^2—CH_2—O\text{-}(AO)_x—CH_2—CH(OH)—R^3 \quad (I).$$

wherein $R^1$ is linear or branched, unsubstituted $C_2$-$C_4$-alkyl, $R^2$ is linear or branched, unsubstituted alkyl group bearing two carbon atoms more than $R^1$, x is an integer in the range of from 10 to 35, AO is identical or different and selected from $CH_2—CH_2—O$, $(CH_2)_3—O$, $(CH_2)_4—O$, $CH_2CH(CH_3)—O$, $CH(CH_3)—CH_2—O—$ and $CH_2CH(n\text{-}C_3H_7)—O$, and $R^3$ is linear or branched, unsubstituted or substituted $C_6$-$C_1$-alkyl.

Mixtures of compounds of general formula (I) are included as well.

In another aspect, the presently claimed invention relates to a process for making a compound of general formula (I) comprising the steps of (a) reacting an alcohol of the formula $R^1—CHR^2—CH_2—OH$ with one or more $C_2$-$C_4$-alkylene oxides, (b) reacting the reaction mixture obtained in step (a) with an epoxide according to formula (II)

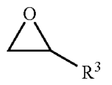

(II)

wherein $R^3$ is as defined above.

In an aspect, the presently claimed invention relates to use of at least one compound of general formula (I) in a composition for automatic dishwashing.

In an aspect, the presently claimed invention relates to a process for cleaning dishware in an automatic dishwasher by using a composition that contains at least one compound of general formula (I).

In an aspect, the presently claimed invention relates to a composition comprising at least one compound of general formula (I) and at least one additive.

DETAILED DESCRIPTION

Before the present compositions and formulations of the invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

If hereinafter a group is defined to comprise at least a certain number of embodiments, this is meant to also encompass a group which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(A)", "(B)" and "(C)" or "(a)", "(b)", "(c)", "(d)", "i", "ii" etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the presently claimed invention. Thus, appearances of the phrases "in one embodiment" or "in an embodiment" or "in another embodiment" in various places throughout this specification are not necessarily all referring to the same embodiment but may do so. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the invention, and form different embodiments, as would be understood by those in the art. For example, in the appended claims, any of the claimed embodiments can be used in any combination.

In one aspect, the presently claimed invention is directed to a compound according to general formula (I)

$R^1$—$CHR^2$—$CH_2$—O-$(AO)_x$—$CH_2$—CH(OH)—$R^3$ (I).

wherein $R^1$ is linear or branched, unsubstituted $C_2$-$C_4$-alkyl, $R^2$ is linear or branched, unsubstituted alkyl group bearing two carbon atoms more than $R^1$, x is an integer in the range of from 10 to 35, AO is identical or different and selected from $CH_2$—$CH_2$—O, $(CH_2)_3$—O, $(CH_2)_4$—O, $CH_2CH(CH_3)$—O, $CH(CH_3)$—$CH_2$—O— and $CH_2CH(n\text{-}C_3H_7)$—O, and $R^3$ is linear or branched, unsubstituted or substituted $C_6$-$C_{18}$-alkyl.

In an embodiment, $R^1$ is selected from the group consisting of ethyl, n-propyl, iso-propyl, n-butyl, sec-butyl and iso-butyl.

In a preferred embodiment, $R^1$ is selected from the group consisting of ethyl, n-propyl and iso-propyl.

In an embodiment, $R^2$ is selected from the group consisting of n-butyl, iso-butyl, n-pentyl, iso-pentyl, 3-methylpentyl, n-hexyl and iso-hexyl.

In an embodiment, x is an integer in the range of from 10 to 35,

In a preferred embodiment, x is an integer in the range of 20 to 30.

In a more preferred embodiment, x is an integer in the range of 22 to 30.

In the context of the present invention, the variable x is to be understood an average number, such average referring to the number average.

In an embodiment, AO is identical or different and selected from $CH_2$—$CH_2$—O, $(CH_2)_3$—O, $(CH_2)_4$—O and $CH_2CH(CH_3)$—O In a more preferred embodiment, AO is $CH_2$—$CH_2$—O.

In one embodiment, $(AO)_x$ is $(CH_2CH_2O)_{x1}$, $x_1$ being selected from 10 to 35.

In an embodiment, identical or different, preferably selected from $CH_2$—$CH_2$—O, $(CH_2)_3$—O, $(CH_2)_4$—O, $CH_2CH(CH_3)$—O, $CH(CH_3)$—$CH_2$—O— and $CH_2CH(n\text{-}C_3H_7)$—O. Preferred example of AO is $CH_2$—$CH_2$—O ("EO").

In one embodiment of the present invention, AO is $(PO)_y$-$(EO)_{x-y}$ and y is an integer in the range of from 0.2 to 2, y being an average value, preferably the number average. In a preferred embodiment, AO is PO-$(EO)_{x-1}$.

In one embodiment of the present invention, $(AO)_x$ is selected from —$(CH_2CH_2O)_{x2}$—$(CH_2CH(CH_3)$—$O)_x$3 and —$(CH_2CH_2O)_{x2}$—$(CH(CH_3)CH_2$—$O)_{x3}$, x2 and x3 being identical or different and selected from 1 to 30, the sum of x2 and x3 being in the range of from 10 to 35.

In one embodiment of the present invention, $(AO)_x$ is selected from —$(CH_2CH_2O)_{x4}$, x4=being in the range of from 10 to 35, all AO being EO, $R^1$ is n-$C_3H_7$ and $R^2$ is n-$C_5H_{11}$.

In another embodiment of the present invention, $(AO)_x$ is selected from —$(CH_2CH_2O)_{x4}$, x4=being in the range of from 10 to 35, all AO being EO, $R^1$ is iso-$C_3H_7$ and $R^2$ is pentyl with at least one methyl branching.

In the context of the present invention, x or $x_1$ or $x_2$ and $x_3$ or x4 are to be understood as average values, the number average being preferred. Therefore, each x or x1 or x2 or x3 or x4—if applicable—can refer to a fraction although a specific molecule can only carry a whole number of alkylene oxide units.

In an embodiment, $R^3$ is selected from the group consisting of n-hexyl, iso-hexyl, n-heptyl, iso-heptyl, n-octyl, iso-octyl, n-nonyl, iso-nonyl, n-decyl, n-dodecyl, n-tetradecyl, n-hexadecyl and n-octadecyl.

In a preferred embodiment, $R^3$ is selected from the group consisting of n-hexyl, n-octyl, n-decyl, n-dodecyl, n-tetradecyl, n-hexadecyl and n-octadecyl.

In a preferred embodiment, $R^3$ is selected from the group consisting of n-hexyl, n-octyl, n-decyl and n-dodecyl.

In another preferred embodiment, $R^3$ is selected from the group consisting of n-decyl and n-dodecyl.

In one embodiment of the present invention, $R^2$ is a mixture of n-$C_5H_{11}$ and pentyl with one branching, for example 2-methylbutyl or 3-methylbutyl, and $R^1$ is n-propyl.

In a preferred embodiment, $R^1$ is n-propyl and $R^2$ is a mixture of n-$C_5H_{11}$ and $C_5H_{11}$ with one branching in a molar range of from 99:1 to 4:1.

In one embodiment, the melting point of the compound of general formula (I) is in the range of from 25 to 40° C., determined according to EN ISO 6321.

In a preferred embodiment, the melting point of the compound of general formula (I) is in the range of from 28 to 33° C.

Inventive compounds are well suited for cleaning dishware, especially in an automatic dishwasher process.

A further aspect of the present invention relates to a method for preparing compound of general formula (I), hereinafter also referred to as inventive manufacturing process. The inventive manufacturing process includes the following steps:

(a) reacting an alcohol of formula $R^1$—$CHR^2$—$CH_2$—OH with one or more $C_2$-$C_4$-alkylene oxides, hereinafter also referred to as step (a), and (b) reacting the reaction mixture obtained in step (a) with an epoxide according to formula (II)

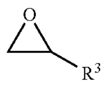

(II)

wherein $R^3$ is $C_6$-$C_{18}$-alkyl, said step hereinafter also referred to as step (b).

The variables $R^1$, $R^2$ and $R^3$ are defined as above.

Steps (a) and (b) may be performed with or without solvent. Examples of suitable organic solvents are nonpolar and polar aprotic organic solvents. Examples of particularly suitable nonpolar aprotic solvents include aliphatic and aromatic hydrocarbons such as hexane, cyclohexane, toluene and xylene. Examples of particularly suitable polar aprotic solvents are ethers, in particular cyclic ethers such as tetrahydrofuran and 1,4-dioxane, furthermore N,N-dialkylamides such as dimethylformamide and dimethylacetamide, and N-alkyllactams such as N-methylpyrrolidone. It is as well possible to use mixtures of at least two of the above organic solvents. Preferred organic solvents are xylene and toluene.

In one embodiment of the present invention, at least one of steps (a) and (b) is performed in bulk. In a preferred embodiment, steps (a) and (b) are both performed in bulk.

In one embodiment of the present invention, step (a) is carried out in the presence of a base. Suitable bases such as potassium hydroxide, sodium hydroxide, sodium or potassium alkoxides such as potassium methylate ($KOCH_3$), potassium tert-butoxide, sodium ethoxide and sodium methylate ($NaOCH_3$), preferably from potassium hydroxide and sodium hydroxide. Further examples of catalysts are alkali metal hydrides and alkaline earth metal hydrides such as sodium hydride and calcium hydride, and alkali metal carbonates such as sodium carbonate and potassium carbonate. Preference is given to the alkali metal hydroxides, preference being given to potassium hydroxide and sodium hydroxide, and to alkali metal alkoxides, particular preference being given to potassium t-butoxide in t-butanol, sodium n-hexanolate in n-hexanol, and to sodium methanolate in n-nonanol. Typical use amounts for the base are from 0.05 to 10% by weight, in particular from 0.5 to 2% by weight, based on the total amount of $R^1$—$CHR^2$—$CH_2$—OH.

In one embodiment of the present invention, step (a) is carried out in the presence of a double-metal cyanide. Double-metal cyanides, hereinafter also referred to as double metal cyanide compounds or DMC compounds, usually comprise at least two different metals, at least one of them being selected from transition metals and the other one being selected from transition metals and alkali earth metals, and furthermore cyanide counterions. Particularly suitable catalysts for the alkoxylation are double-metal cyanide compounds which contain zinc, cobalt or iron or two thereof. Berlin blue, for example, is particularly suitable.

Preference is given to using crystalline DMC compounds. In a preferred embodiment, a crystalline DMC compound of the Zn—Co type which comprises zinc acetate as further metal salt component is used as catalyst. Such compounds crystallize in monoclinic structure and have a platelet-like habit.

In one embodiment of the present invention, step (a) is carried out in the presence of at least one double-metal cyanide selected from hexacyano cobaltates.

Preferably, though, step (a) is carried out in the absence of a base and in the absence of any catalyst.

In one embodiment of the present invention, step (a) is carried out at a reaction temperature in the range of from 70 to 250° C. and preferably from 140 to 200° C.

In one embodiment of the present invention, step (a) is carried out at a pressure of up to 10 bar and in particular up to 8 bar, for example 2 to 4 bar.

In one embodiment of the present invention, the reaction time of step (a) is generally in the range of from 0.5 to 12 hours, preferred are 1 to 6 hours.

In step (b), the product obtained from step (a) is reacted with at least one epoxide according to formula (II).

In one embodiment of the present invention, step (b) is carried out in the presence of a catalyst, for example a base or a double-metal cyanide. Double-metal cyanides, hereinafter also referred to as double metal cyanide compounds or DMC compounds, usually comprise at least two different metals, at least one of them being selected from transition metals and the other one being selected from transition metals and alkali earth metals, and furthermore cyanide counterions. Particularly suitable catalysts for the alkoxylation are double-metal cyanide compounds which contain zinc, cobalt or iron or two thereof. Berlin blue, for example, is particularly suitable. It is preferred, though, to perform step (b) without any catalyst.

In one embodiment of the present invention, step (b) of the inventive process is carried out in the presence of a base. Suitable bases such as potassium hydroxide, sodium hydroxide, sodium or potassium alkoxides such as potassium methylate ($KOCH_3$), potassium tert-butoxide, sodium ethoxide and sodium methylate ($NaOCH_3$), preferably from potassium hydroxide and sodium hydroxide. Further examples of catalysts are alkali metal hydrides and alkaline earth metal hydrides such as sodium hydride and calcium hydride, and alkali metal carbonates such as sodium carbonate and potassium carbonate. Preference is given to the alkali metal hydroxides, preference being given to potassium hydroxide and sodium hydroxide, and to alkali metal alkoxides, particular preference being given to potassium t-butoxide in t-butanol, sodium n-hexanolate in n-hexanol, and to sodium methanolate in n-nonanol. Typical use amounts for the base are from 0.01 to 0.1 mole catalyst per moles of alcohol $R^1$—$CHR^2$—$CH_2$—OH, in particular from 0.02 to 0.06 mole/mole, based on the total amount of $R^1$—$CHR^2$—$CH_2$—OH, even more preferred 0.025 to 0.045 mole/mole. It is preferred, though, to perform step (b) without the use of a base.

In one embodiment of the present invention, step (b) is carried out at a reaction temperature in the range of from 120 to 200° C. and preferably from 140 to 180° C. and more preferably 150 to 170° C.

In one embodiment of the present invention, step (b) is carried out at a pressure of up to 10 bar and in particular up to 8 bar, for example 1 to 8 bar. Normal pressure is most preferred.

In one embodiment of the present invention, the reaction time of step (b) is generally in the range of one to 6 hours.

An optional step of work-up may include the deactivation of catalyst used in step (a).

The inventive manufacturing process does not require bleaching steps or reductive removal of impurities.

In one embodiment of the present invention, the product made by the inventive process has a Hazen color number in the range of from 5 to 1,000, preferred are 5 to 500 and even ore preferred 5 to 300, determined according to DIN ISO 6271 ASTM D 1209. The Hazen colour number can preferably be determined by spectrophotometric means on a 10 wt. % aqueous solution.

A further aspect of the present invention relates to the use of an inventive compound or of a combination of at least two inventive compounds in a composition for automatic dishwashing, altogether hereinafter referred to as inventive cleaning process. Another aspect of the present invention relates to a process for cleaning dishware in an automatic dishwasher by using a composition that contains at least one inventive compound or a combination of at least two inventive compounds.

The inventive cleaning process is a process for cleaning dishware. The inventive cleaning process can be carried out with the help of a machine (machine dishwash or automatic dishwash). Dishes in the context of the present invention shall not only refer to plates from china but also to any kitchenware from china, metal, glass, clay or polymer, such as—but not limited to—cups, bowls and plates from china, flatware, drinking glasses such as wine glasses, champagne flutes, beer glasses and the like, and plastic kitchenware, furthermore pots, frying pans and Dutch ovens from metal such as iron, aluminum or stainless steel.

Dishware is provided in soiled form, among other soiled with fatty residue, also referred to as fat, that may stem from food itself or—for example in the case of frying pans—fat that stems from cooking or frying or baking food. The term "fat" may also include lard or oil, especially oil like sunflower oil, olive oil or other oil that is used for cooking purposes.

Said fatty residue may be the sole soiling of dishware to be cleaned according to the inventive cleaning process. In another embodiment of the present invention, dishware to be cleaned according to inventive cleaning process may be soiled with a combination of fat and at least one substance other than fat, for example pigment(s), protein, carbohydrates such as starch or sugar, caramel, furthermore lecithin, or dyestuff(s).

On the dishware may a coherent layer of soiling, or—in other embodiments—only one or more spots or limited areas of the respective dishware may be soiled.

The inventive cleaning process is being carried out at temperatures in the range of from 40 to 65° C., preferably 45 to 60° C. Said temperature refers to the temperature of the water being used in the inventive cleaning process. The inventive cleaning process is being described in more detail below.

The inventive cleaning process is being carried out using water. The amount of water is influenced by the type of machine used and by the choice of the program.

In an aspect, the presently claimed invention is directed to a cleaning composition comprising (A) at least one compound of general formula (I), and (B) at least one additive;

Such cleaning compositions are hereinafter also referred to as inventive compositions.

At room temperature, the cleaning composition may be solid, liquid or gel type, and it may be in bulk or in a unit dose format.

The cleaning composition of the presently claimed invention are particularly efficient if they contain at least one additive, such as a builder that is capable to remove alkali earth metal cations, for example a chelating agent such as citric acid or an alkali metal salt of citric acid. It is preferred, thus, that the cleaning compositions comprise at least one compound of general formula (I) and at least one additive such as a chelating agent, for example aminocarboxylic acid diacetate or an alkali metal salt thereof.

In one embodiment, the presently claimed invention is directed to a cleaning composition comprising (A) 0.5 to 10% by weight of at least one compound of general formula (I), and (B) 1 to 50% by weight of at least one additive;

by weight of the final weight of the cleaning composition.

Percentages refer to the total solids content of the respective inventive composition.

In another embodiment, the presently claimed invention is directed to the cleaning composition comprising (A) 1 to 8% by weight of at least one compound of general formula (I), and (B) 2 to 45% by weight of at least one additive;

by weight of the final weight of the cleaning composition.

In another embodiment of the present invention, the presently claimed invention is directed to the cleaning composition comprising (A) 2 to 6% by weight of at least one compound of general formula (I), and (B) 5 to 40% by weight of at least one additive;

by weight of the final weight of the cleaning composition.

Additives

The cleaning composition according to the present invention may further comprise additives such as Chelating agents, enzymes, builders, cobuilders, alkali metal carriers, bleaching agents, bleach catalysts, bleach activators, dyes, perfumes, corrosion inhibitors, anti-redeposition agents and fillers.

Chelating Agents

The composition according to the invention may include a chelating/sequestering agent such as an aminocarboxylic acid, a condensed phosphate, a phosphonate and a polyacrylate. In general, a chelating agent is a molecule capable of coordinating (i.e., binding) the metal ions commonly found in natural water to prevent the metal ions from interfering with the action of the other detersive ingredients of the dishwashing composition. Useful aminocarboxylic acids include, for example, n-hydroxyethyliminodiacetic acid, nitrilotriacetic acid (NTA), ethylenediaminetetraacetic acid (EDTA), N-hydroxyethyl ethylenediaminetriacetic acid (HEDTA), diethylenetriamine pentaacetic acid (DTPA), methylglycinediacetic acid (MGDA) and glutamic acid diacetic acid (GLDA). Examples of condensed phosphates are sodium and potassium orthophosphate, sodium and potassium pyrophosphate, sodium tripolyphosphate and sodium hexametaphosphate.

Aminocarboxylic acid diacetates are compounds with at least one amino group that is carboxy-alkylated with two $CH_2$—COOH groups. Aminosuccinates are compounds with at least one nitrogen atom per molecule that bears a $CH(COOH)CH_2COOH$ group. In each case, the respective alkali metal salts are preferred over their respective free acids In a preferred embodiment of the present invention inventive compositions aminocarboxylic acid diacetates are selected from methylglycine diacetic acid (MGDA), and glutamic acid diacetic acid (GLDA).

In inventive automatic detergent compositions, MGDA and GLDA are comprised in the form of alkali metal salts, for example in the form of potassium salts or sodium salts or as mixed sodium-potassium salts.

Preferred alkali metal salts of MGDA are compounds according to the general formula (III a)

$$[CH_3\text{—}CH(COO)\text{—}N(CH_2\text{—}COO)_2]M^1_{3-r}H_r \quad \text{(III a)}$$

wherein $M^1$ is selected from alkali metal cations, same or different, preferably potassium and especially sodium, and wherein r is in the range of from zero to 0.5.

Preferred alkali metal salts of GLDA are compounds according to the general formula (III a)

$$[OOC\text{—}CH_2CH_2\text{—}CH(COO)\text{—}N(CH_2\text{—}COO)_2]M^1_{4-r}H_r \quad \text{(III b)}$$

Wherein r is in the range of from zero to 1.5, and $M^1$ is defined as above.

It is to be understood that r is an average number.

Compounds according to general formula (III a) and (III b) may be comprised as racemic mixture or as pure enantiomers, especially as L-enantiomers, or as non-racemic mixtures of enantiomers, for example with an enantiomeric excess in the range of from 20 to 85%, the respective L-enantiomer being the predominant enantiomer.

Particularly preferred are racemic mixtures of the trisodium salt of MGDA, racemic mixture or non-racemic mixtures of enantiomers wherein the L-enantiomer prevails, with an enantiomeric excess in the range of from 20 to 85%. Another particularly preferred embodiment is the tetrasodium salt of GLDA as non-racemic mixtures of enantiomers wherein the L-enantiomer prevails, with an enantiomeric excess in the range of from 20 to 99.5%. Another particularly preferred embodiment are mixtures of the trisodium and the tetrasodium salts of GLDA each as non-racemic mixtures of enantiomers wherein the L-enantiomers prevail, with enantiomeric excesses in the range of from 20 to 99.5%.

Compounds according to general formula (III a) and (III b) may contain impurities resulting from their synthesis. In the case of MGDA and its alkali metal salts, such impurities may include propionic acid, lactic acid, alanine, nitrilotriacetic acid (NTA) or the like and their respective alkali metal salts, and complexes of $Mg^{2+}$, $Ca^{2+}$, Fe(II+) and Fe(III+). Such impurities are usually present in minor amounts. “Minor amounts” in this context refer to a total of 0.1 to 5% by weight, referring to alkali metal salt of chelating agent (B), preferably up to 2.5% by weight. In the context of the present invention, such minor amounts are neglected when determining the composition of the respective detergent composition according to the present invention.

The chelating agent may be citric acid or an alkali metal salt of citric acid.

Enzymes

Inventive compositions may comprise one or more enzymes. Enzymes are often used to aid the removal of stains. In most cases the enzymes react with the soiling and break it down into particles that have increased water solubility or are better dispersible in the washing liquid. The enzymes that can be used in dishwashing compositions include, but are not limited to, hydrolases, proteases, amylases, lipases, cellulases, mannanase, peroxidase, oxidase, xylanase, pullulanase, glucanase, pectinase, cutinase, hemicellulases, glucoamylases, phospholipases, esterases, keratanases, reductases, phenoloxidases, lipoxygenases, ligninases, tannases, pentosanases, malanases, arabinosidases, hyaluronidase, chondroitinase, lactases or mixtures thereof.

In one embodiment of the present invention, inventive compositions may comprise, for example, up to 5% by weight of enzyme, preference being given to 0.1 to 3% by weight. Said enzyme may be stabilized, for example with the sodium salt of at least one $C_1$-$C_3$-carboxylic acid or $C_4$-$C_{10}$-dicarboxylic acid. Preferred are formates, acetates, adipates, and succinates.

Builders

The dishwashing compositions may comprise one or more builders, selected from organic and inorganic builders. Examples of suitable inorganic builders are sodium sulfate or sodium carbonate or silicates, in particular sodium disilicate and sodium metasilicate, zeolites, sheet silicates, in particular those of the formula α-$Na_2Si_2O_5$, β-$Na_2Si_2O_5$, and δ-$Na_2Si_2O_5$, also fatty acid sulfonates, α-hydroxypropionic acid, alkali metal malonates, fatty acid sulfonates, alkyl and alkenyl disuccinates, tartaric acid diacetate, tartaric acid monoacetate, oxidized starch, and polymeric builders, for example polycarboxylates and polyaspartic acid.

Examples of organic builders are especially polymers and copolymers. In one embodiment of the present invention, organic builders are selected from polycarboxylates, for example alkali metal salts of (meth)acrylic acid homopolymers or (meth)acrylic acid copolymers.

Suitable comonomers are monoethylenically unsaturated dicarboxylic acids such as maleic acid, fumaric acid, maleic anhydride, itaconic acid and citraconic acid. A suitable polymer is in particular polyacrylic acid, which preferably has an average molecular weight $M_w$ in the range from 2000 to 40 000 g/mol, preferably 2000 to 10 000 g/mol, in particular 3000 to 8000 g/mol. Also, of suitability are copolymeric polycarboxylates, in particular those of acrylic acid with methacrylic acid and of acrylic acid or methacrylic acid with maleic acid and/or fumaric acid, and in the same range of molecular weight.

It is also possible to use copolymers of at least one monomer from the group consisting of monoethylenically unsaturated $C_3$-$C_{10}$-mono- or $C_4$-$C_{10}$-dicarboxylic acids or anhydrides thereof, such as maleic acid, maleic anhydride, acrylic acid, methacrylic acid, fumaric acid, itaconic acid and citraconic acid, with at least one hydrophilic or hydrophobic monomer as listed below.

Suitable hydrophobic monomers are, for example, isobutene, diisobutene, butene, pentene, hexene and styrene, olefins with 10 or more carbon atoms or mixtures thereof, such as, for example, 1-decene, 1-dodecene, 1-tetradecene, 1-hexadecene, 1-octadecene, 1-eicosene, 1-docosene, 1-tetracosene and 1-hexacosene, $C_{22}$-α-olefin, a mixture of $C_{20}$-$C_{24}$-α-olefins and polyisobutene having on average 12 to 100 carbon atoms per molecule.

Suitable hydrophilic monomers are monomers with sulfonate or phosphonate groups, and also nonionic monomers with hydroxyl function or alkylene oxide groups. By way of example, mention may be made of: allyl alcohol, isoprenol, methoxypolyethylene glycol (meth)acrylate, methoxypolypropylene glycol (meth)acrylate, methoxypolybutylene glycol (meth)acrylate, methoxypoly(propylene oxide-co-ethylene oxide) (meth)acrylate, ethoxypolyethylene glycol (meth)acrylate, ethoxypolypropylene glycol (meth)acrylate, ethoxypolybutylene glycol (meth)acrylate and ethoxypoly(propylene oxide-co-ethylene oxide) (meth) acrylate. Polyalkylene glycols here may comprise 3 to 50, in particular 5 to 40 and especially 10 to 30 alkylene oxide units per molecule.

Particularly preferred sulfonic-acid-group-containing monomers here are 1-acrylamido-1-propanesulfonic acid, 2-acrylamido-2-propanesulfonic acid, 2-acrylamido-2-methylpropanesulfonic acid, 2-methacrylamido-2-methylpropanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, vinylsulfonic acid, 3-sulfopropyl acrylate, 2-sulfoethyl methacrylate, 3-sulfopropyl methacrylate, sulfomethacrylamide, sulfomethylmethacrylamide, and salts of said acids, such as sodium, potassium or ammonium salts thereof.

Particularly preferred phosphonate-group-containing monomers are vinylphosphonic acid and its salts.

A further example of builders is carboxymethyl inulin.

Moreover, amphoteric polymers can also be used as builders.

Inventive compositions may comprise, for example, in the range from in total 10 to 70% by weight, preferably up to 50% by weight, of builder.

Cobuilders

The dishwashing compositions may comprise cobuilders. Examples of cobuilders are phosphonates, for example hydroxyalkanephosphonates and aminoalkanephosphonates. Hydroxyalkanephosphonates such as 1-hydroxyethane-1,1-diphosphonate (HEDP) is preferably used as the sodium salt, the disodium salt being neutral and the tetrasodium salt being alkaline (pH 9). Suitable aminoalkanephosphonates are preferably ethylenediaminetetramethylenephosphonate (EDTMP), diethylenetriaminepentamethylenephosphonate (DTPMP) and also higher homologs thereof. They are preferably used in the form of the neutrally reacting sodium salts, e.g. as the hexasodium salt of EDTMP or as the hepta- and octasodium salts of DTPMP.

Alkali Metal Carriers

The dishwashing composition according to the present invention may comprise one or more alkali metal carriers. Alkali metal carriers provide, for example, a pH of at least 9, if an alkaline pH is desired. For example, alkali metal carbonates, alkali metal hydrogen carbonates, alkali metal hydroxides and alkali metal metasilicates are suitable alkali metal carriers.

Bleaching Agents

The dishwashing composition of the present invention may optionally comprise one or more bleaching agents. The bleaching agents can be used in a detergent composition either alone or in combination with a bleach activator and/or a bleach catalyst. The function of the bleaching agent is the removal of bleachable stains and to achieve an antibacterial effect on the load and inside of the dishwashing machine. Bleaching agents commonly used as a sole bleaching ingredient in dishwashing composition react with the soil. When an inorganic oxygen based bleaching agent is used in combination with a bleach activator it does react with the bleach activator. One of the reaction products provides the actual performance. When an inorganic oxygen based bleaching agent is used in combination with a bleach catalyst, the catalyst catalyses the oxidation reaction with the substrate. The oxidized bleach catalyst provides the actual bleach performance. A bleach activator can optionally be present.

Bleaching agents may be selected from chlorine bleach and peroxide bleach, and peroxide bleach may be selected from inorganic peroxide bleach and organic peroxide bleach. Preferred are inorganic peroxide bleaches, selected from alkali metal percarbonate such as sodium percarbonate, alkali metal perborate and alkali metal persulfate.

Examples of organic peroxide bleaches are organic percarboxylic acids, especially organic percarboxylic acids.

In inventive compositions, alkali metal percarbonates, especially sodium percarbonates, are preferably used in coated form. Such coatings may be of organic or inorganic nature. Examples are glycerol, sodium sulfate, silicate, sodium carbonate, and combinations of at least two of the foregoing, for example combinations of sodium carbonate and sodium sulfate.

Suitable chlorine-containing bleaches are, for example, 1,3-dichloro-5,5-dimethylhydantoin, N-chlorosulfamide, chloramine T, chloramine B, sodium hypochlorite, calcium hypochlorite, magnesium hypochlorite, potassium hypochlorite, potassium dichloroisocyanurate and sodium dichloroisocyanurate.

Inventive compositions may comprise, for example, in the range from 3 to 10% by weight of chlorine-containing bleach.

Bleach Catalysts

A bleaching catalyst can be used besides to or instead of a bleach activator. Bleach catalysts can be selected from bleach-boosting transition metal salts or transition metal complexes such as, for example, manganese-, iron-, cobalt-, ruthenium- or molybdenum-salen complexes or carbonyl complexes. Manganese, iron, cobalt, ruthenium, molybdenum, titanium, vanadium and copper complexes with nitrogen-containing tripod ligands and also cobalt-, iron-, copper- and rutheniumamine complexes can also be used as bleach catalysts.

Complexes including these metals can interact with inorganic and organic peroxygen compounds to form reactive intermediates. The use of a bleach catalyst can result in achieving the desired bleaching performance at an even lower temperature than needed for bleach activators. Bleaching catalysts include, but are not limited to a complex of manganese (IV) with 1,4,7-trimethyl-1,4,7-triazacyclononane (MnMe3TACN), tris[2-(salicylideneamino)ethyl] amine manganese(III), siderophore-metal complexes, metal complexes containing ligands of 1,4,7-triazacyclononan (TACN), manganese-protein complexes.

Bleach Activators

Inventive compositions may comprise one or more bleach activators. Bleaching agents that can be used in detergent compositions include, but are not limited to, tetraacetylethylenediamine (TAED), tetraacetylhexylenediamine, sodium nonanoyloxybenzene sulfonate (NOBS), acetyl caprolactone, N-methyl morpholinium acetonitrile salts ("MMA salts"), and salts thereof, sodium 4-(2-decanoyl oxyethoxycarbonyloxy) benzenesulfonate (DECOBS), trimethylammonium acetonitrile salts, N-acylimides such as, for example, N-nonanoylsuccinimide, 1,5-diacetyl-2,2-dioxohexahydro-1,3,5-triazine ("DADHT") or nitrile quats (trimethylammonium acetonitrile salts).

Dyes

The composition of the present invention may optionally comprise one or more dyes. The dye is used to colour the dishwashing composition. This might render the product more attractive to the consumer. Dyes that can be used in dishwashing composition include, but are not limited to, Nylosan yellow N-7GL, Sanolin brilliant flavine 8GZ, Sanolin yellow BG, Vitasyn quinoline yellow 70, Vitasyn tartrazine X90, Puricolor yellow AYE23, Basacid yellow 232, Vibracolor yellow AYE17, Simacid Eosine Y, Puricolor red ARE27, Puricolor red ARE14, Vibracolor red ARE18, Vibracolor red ARE52, Vibracolor red SRE3, Basacid red 316, Ponceau SX, Iragon blue DBL86, Sanolin blue EHRL, Sanolin turquoise blue FBL, Basacid blue 750, Iragon blue ABL80, Vitasyn blue AE90, Basacid blue755, Vitasyn patentblue V 8501 and Vibracolor green AGR25.

Perfumes

The dishwashing composition may optionally comprise one or more perfumes. Perfume is added to the dishwashing composition to improve the sensorial properties of the product or of the dishwasher after cleaning. The perfume can be added to the detergent as a liquid, paste or as a cogranulate with a carrier material for the perfume. To improve the stability of the perfume it can be used in an encapsulated form or as a complex like for example a perfume-cyclodextrine complex. Also perfumes that have a deodorizing effect can be applied. Such perfumes or raw materials encapsulate malodours by binding to their sulphur groups.

Corrosion Inhibitors

Inventive compositions may comprise one or more corrosion inhibitors. In the present case, this is to be understood as including those compounds that inhibit the corrosion of metal. Examples of suitable corrosion inhibitors are triazoles, in particular benzotriazoles, bisbenzotriazoles, aminotriazoles, alkylaminotriazoles, also phenol derivatives such as, for example, hydroquinone, pyrocatechol, hydroxyhydroquinone, gallic acid, phloroglucinol or pyrogallol.

In one embodiment of the present invention, inventive compositions comprise in total in the range from 0.1 to 1.5% by weight of corrosion inhibitor.

Anti-Redeposition Agents

The dishwashing composition may optionally comprise one or more anti-redeposition agents. The main function of anti-redeposition agents is the aid to prevent the soil from redepositing on the washing substrate when a washing liquor provides insufficient soil anti-redeposition capacity. Anti-redeposition agent(s) can provide their effect by becoming adsorbed irreversibly or reversibly to the soil particles or to the substrate, thereby the soil becomes better dispersed in the washing liquor or the substrate is occupied with anti-redeposition agent(s) on those places the soil could redeposit. The anti-redeposition agent(s) that are known to be used in dishwashing compositions include, but are not limited to, carboxymethyl cellulose, polyester-PEG co-polymer, polyvinyl pyrrolidone based polymers.

Fillers

An inert particulate filler material which is water-soluble may also be present in the dishwashing compositions in powder form. This material should not precipitate calcium or magnesium ions at the filler use level. Suitable for this purpose are organic or inorganic compounds. Organic fillers include sucrose esters and urea. Representative inorganic fillers include sodium sulfate, sodium chloride and potassium chloride.

Surfactants

Examples of such surfactants other than inventive compound are especially non-ionic surfactants other than inventive compound.

Preferred non-ionic surfactants are alkoxylated alcohols, di- and multiblock copolymers of ethylene oxide and propylene oxide and reaction products of sorbitan with ethylene oxide or propylene oxide, alkyl polyglycosides (APG), hydroxyalkyl mixed ethers and amine oxides.

Preferred examples of alkoxylated alcohols and alkoxylated fatty alcohols are, for example, compounds of the general formula (IV)

(IV)

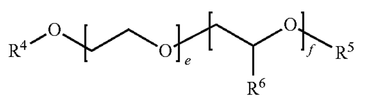

in which the variables are defined as follows:

$R^4$ is selected from $C_8$-$C_{22}$-alkyl, branched or linear, for example n-$CH_{17}$, n-$C_{10}H_{21}$, n-$C_{12}H_{25}$, n-$C_{14}H_{29}$, n-$C_{16}H_{33}$ or n-$C_{18}H_{37}$, $R^5$ is selected from $C_1$-$C_{10}$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl or isodecyl, $R^6$ is identical or different and selected from hydrogen and linear $C_1$-$C_{10}$-alkyl, preferably in each case identical and ethyl and particularly preferably hydrogen or methyl, The variables e and f are in the range from zero to 300, where the sum of e and f is at least one, preferably in the range of from 3 to 50. Preferably, e is in the range from 1 to 100 and f is in the range from 0 to 30.

In one embodiment, compounds of the general formula (IV) may be block copolymers or random copolymers, preference being given to block copolymers.

Other preferred examples of alkoxylated alcohols are, for example, compounds of the general formula (V)

(V)

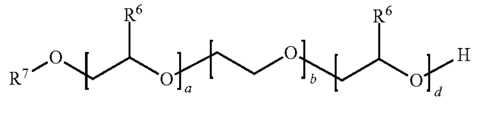

in which the variables are defined as follows:

$R^6$ is identical or different and selected from hydrogen and linear $C_1$-$C_4$-alkyl, preferably identical in each case and ethyl and particularly preferably hydrogen or methyl, $R^7$ is selected from $C_6$-$C_{20}$-alkyl, branched or linear, in particular n-$CH_{17}$, n-$C_{10}H_{21}$, n-$C_{12}H_{25}$, n-$C_{13}H_{27}$, n-$C_{15}H_{31}$, n-$C_{14}H_{29}$, n-$C_{16}H_{33}$, n-$C_{18}H_{37}$, and combinations of at least two of the foregoing, a is a number in the range from zero to 10, preferably from 1 to 6, b is a number in the range from 1 to 80, preferably from 4 to 20, d is a number in the range from zero to 50, preferably 4 to 25.

The sum a+b+d is preferably in the range of from 5 to 100, even more preferably in the range of from 9 to 50.

The variables m and n are in the range from zero to 300, where the sum of n and m is at least one, preferably in the range of from 5 to 50. Preferably, m is in the range from 1 to 100 and n is in the range from 0 to 30.

Another class of non-ionic surfactants are hydroxyl group bearing compounds other than compound (1). Preferred examples of hydroxyl group bearing compounds are compounds of the general formula (VI)

(VI)

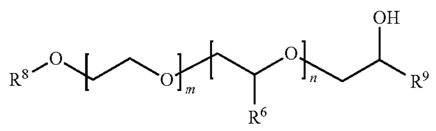

in which the variables are defined as follows:

$R^6$ is identical or different and selected from hydrogen and linear $C_1$-$C_{10}$-alkyl, preferably in each case identical and ethyl and particularly preferably hydrogen or methyl, $R^8$ is selected from $C_8$-$C_{22}$-alkyl, branched or preferably linear, for example iso-$C_{11}H_{23}$, iso-$C_{13}H_{27}$, n-$CH_{17}$, n-$C_{10}H_{21}$, n-$C_{12}H_{25}$, n-$C_{14}H_{29}$, n-$C_{16}H_{33}$ or n-$C_{18}H_{37}$, $R^9$ is selected from $C_1$-$C_{13}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, isodecyl, n-dodecyl, n-tetradecyl, n-hexadecyl, and n-octadecyl.

The variables m and n are in the range from zero to 300, where the sum of n and m is at least one, preferably in the range of from 5 to 50. Preferably, n is in the range from 1 to 100 and m is in the range from 0 to 30.

In a special version, hydroxyl group bearing compounds are compounds of the general formula (VI a)

$$R^9—CH(OH)—CH_2—O\text{-}(AO)_r\text{-}A^1\text{-}O\text{-}(AO)_r—CH_2—CH(OH)—R^9 \quad \text{(VI a)}$$

wherein $R^9$ are same or different and defined as above, r same or different and selected from 6 to 50, preferably 12 to 25. In compounds according to general formula (I b), it is preferred that both r assume the same value.

$A^1$ is selected from $C_2$-$C_{10}$-alkylene, straight chain or branched, for example—$CH_2$—$CH_2$—, —$CH_2$—$CH(CH_3)$—, —$CH_2$—$CH(CH_2CH_3)$—, —$CH_2$—CH(n-$C_3H_7$)—, —$CH_2$—CH(n-$C_4H_9$)—, —$CH_2$—CH(n-$C_5H_{11}$)—, —$CH_2$—CH(n-$C_6H_{13}$)—, —$CH_2$—CH(n-$C_8H_{17}$)—, —$CH(CH_3)$—$CH(CH_3)$—, —$(CH_2)_3$—, —$(CH_2)_4$—, —$(CH_2)_5$—, —$(CH_2)_6$—, —$(CH_2)_8$—, —$(CH_2)_{10}$—, —$C(CH_3)_2$—, —$CH_2$—$C(CH_3)_2$—$CH_2$—, and —$CH_2$—$[C(CH_3)_2]_2$—$CH_2$—.

Preferred residues $A^1$ are —$CH_2$—$CH_2$—, —$CH_2$—$CH(CH_3)$—, —$CH_2$—$CH(CH_2CH_3)$—, —$CH_2$—CH(n-$C_3H_7$)—, —$CH_2$—CH(n-$C_4H_9$)—, —$CH_2$—CH(n-$C_6H_{13}$)—, and —$(CH_2)_4$—.

Compounds of the general formula (IV), (V) and (VI) and especially (VI a) may be block copolymers or random copolymers, preference being given to block copolymers.

Further suitable nonionic surfactants are selected from di- and multiblock copolymers, composed of ethylene oxide and propylene oxide. Further suitable nonionic surfactants are selected from ethoxylated or propoxylated sorbitan esters. Amine oxides or alkyl polyglycosides, especially linear $C_4$-$C_{16}$-alkyl polyglucosides and branched $C_8$-$C_{14}$-alkyl polyglycosides such as compounds of general average formula (VII) are likewise suitable.

(VII)

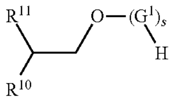

wherein:

$R^{10}$ is $C_1$-$C_4$-alkyl, in particular ethyl, n-propyl or iso-propyl, or hydrogen, $R^{11}$ is —$(CH_2)_2$—$R^{10}$, or n-$C_7$-$C_{12}$-alkyl, $G^1$ is selected from monosaccharides with 4 to 6 carbon atoms, especially from glucose and xylose, s in the range of from 1.1 to 4, s being an average number, Further examples of non-ionic surfactants are compounds of general formula (VIII) and (IX)

(III)

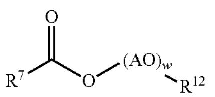

(IX)

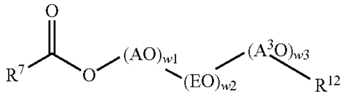

$R^7$ and AO are defined as above, $R^{12}$ selected from $C_5$-$C_{18}$-alkyl, branched or linear.

$A^3O$ is selected from propylene oxide and butylene oxide, w is a number in the range of from 15 to 70, preferably 30 to 50, w1 and w3 are numbers in the range of from 1 to 5, and w2 is a number in the range of from 13 to 35.

An overview of suitable further nonionic surfactants can be found in EP-A 0 851 023 and in DE-A 198 19 187.

Mixtures of two or more different nonionic surfactants selected from the foregoing may also be present.

Inventive compositions may comprise one or more anionic or zwitterionic surfactants.

Examples of amphoteric surfactants are those that bear a positive and a negative charge in the same molecule under use conditions. Preferred examples of amphoteric surfactants are so-called betaine-surfactants. Many examples of betaine-surfactants bear one quaternized nitrogen atom and one carboxylic acid group per molecule. A particularly preferred example of amphoteric surfactants is cocamidopropyl betaine (lauramidopropyl betaine).

Examples of amine oxide surfactants are compounds of the general formula (X)

$$R^{13}R^{14}R^{15}N\rightarrow O \quad \text{(X)}$$

wherein $R^{13}$, $R^{14}$, and $R^{15}$ are selected independently from each other from aliphatic, cycloaliphatic or $C_2$-$C_4$-alkylene $C_{10}$-$C_{20}$-alkylamido moieties. Preferably, $R^{13}$ is selected from $C_5$-$C_{20}$-alkyl or $C_2$-$C_4$-alkylene $C_{10}$-$C_{20}$-alkylamido and $R^{15}$ and $R^{14}$ are both methyl.

A particularly preferred example is lauryl dimethyl aminoxide, sometimes also called lauramine oxide. A further particularly preferred example is cocamidylpropyl dimethylaminoxide, sometimes also called cocamidopropylamine oxide.

Examples of suitable anionic surfactants are alkali metal and ammonium salts of $C_8$-$C_{18}$-alkyl sulfates, of $C_5$-$C_{18}$-fatty alcohol polyether sulfates, of sulfuric acid half-esters of ethoxylated $C_4$-$C_{12}$-alkylphenols (ethoxylation: 1 to 50 mol of ethylene oxide/mol), $C_{12}$-$C_{18}$ sulfo fatty acid alkyl esters, for example of $C_{12}$-$C_{18}$ sulfo fatty acid methyl esters, furthermore of $C_{12}$-$C_{13}$-alkylsulfonic acids and of $C_{10}$-$C_{13}$-alkylarylsulfonic acids. Preference is given to the alkali metal salts of the aforementioned compounds, particularly preferably the sodium salts.

Further examples for suitable anionic surfactants are soaps, for example the sodium or potassium salts of stearic acid, oleic acid, palmitic acid, ether carboxylates, and alkylether phosphates.

In one embodiment of the present invention, inventive compositions may contain 0.1 to 60% by weight of at least one surfactant, selected from anionic surfactants, amphoteric surfactants and amine oxide surfactants.

In a preferred embodiment, inventive compositions do not contain any anionic surfactant.

Antifoam Agents

Inventive compositions may comprise one or more antifoams, selected for example from silicone oils and paraffin oils.

In one embodiment of the present invention, inventive compositions comprise in total in the range from 0.05 to 0.5% by weight of antifoam.

Zinc Salts

In one embodiment of the present invention, inventive compositions, especially when used as automatic dishwashing detergents, may comprise at least one zinc salt. Zinc salts may be selected from water-soluble and water-insoluble zinc salts. In this connection, within the context of the present invention, water-insoluble is used to refer to those zinc salts which, in distilled water at 25° C., have a solubility of 0.1 g/l or less. Zinc salts which have a higher solubility in water are accordingly referred to within the context of the present invention as water-soluble zinc salts.

In one embodiment of the present invention, zinc salt is selected from zinc benzoate, zinc gluconate, zinc lactate, zinc formate, $ZnCl_2$, $ZnSO_4$, zinc acetate, zinc citrate, $Zn(NO_3)_2$, $Zn(CH_3SO_3)_2$ and zinc gallate, preferably $ZnCl_2$, $ZnSO_4$, zinc acetate, zinc citrate, $Zn(NO_3)_2$, $Zn(CH_3SO_3)_2$ and zinc gallate.

In another embodiment of the present invention, zinc salt is selected from ZnO, ZnO·aq, $Zn(OH)_2$ and $ZnCO_3$. Preference is given to ZnO·aq.

In one embodiment of the present invention, zinc salt is selected from zinc oxides with an average particle diameter (weight-average) in the range from 10 nm to 100 μm.

The cation in zinc salt can be present in complexed form, for example complexed with ammonia ligands or water ligands, and in particular be present in hydrated form. To simplify the notation, within the context of the present invention, ligands are generally omitted if they are water ligands.

Depending on how the pH of mixture according to the invention is adjusted, zinc salt can change. Thus, it is for example possible to use zinc acetate or $ZnCl_2$ for preparing formulation according to the invention, but this converts at a pH of 8 or 9 in an aqueous environment to ZnO, $Zn(OH)_2$ or ZnO·aq, which can be present in non-complexed or in complexed form.

Zinc salt may be present in those inventive automatic dishwashing formulations which are solid at room temperature are preferably present in the form of particles which have for example an average diameter (number-average) in the range from 10 nm to 100 μm, preferably 100 nm to 5 μm, determined for example by X-ray scattering.

Zinc salt may be present in those detergent compositions for home care applications that are liquid at room temperature in dissolved or in solid or in colloidal form.

In one embodiment of the present invention, inventive automatic dishwashing formulations comprise in total in the range from 0.05 to 0.4% by weight of zinc salt, based in each case on the solids content of the composition in question.

Here, the fraction of zinc salt is given as zinc or zinc ions. From this, it is possible to calculate the counterion fraction.

Polyalkyleneimine

In one embodiment of the present invention, inventive automatic dishwashing formulation contain polyalkylenimine, for example polypropylenimine or polyethylenimine. Polyalkylenimine may be substituted, for example with $CH_2OOH$ groups or with polyalkylenoxide chains, or non-substituted. In one embodiment of the present invention, 60 to 80 mole-% of the primary and secondary amine functions of polyalkylenimines are substituted with $CH_2OOH$ groups or with ethylene oxide or propylene oxide. Particularly preferred are non-substituted polyethylenimine with an average molecular weight $M_w$ in a range of from 500 to 20,000 g/mol, determined advantageously by gel permeation chromatography (GPC) in 1.5% by weight aqueous formic acid as eluent and cross-linked poly-hydroxyethylmethacrylate as stationary phase. In other embodiments, polyethoxylated polyethylenimines are preferred, with an average molecular weight $M_w$ in a range of from 2,500 to 50,000 g/mol, determined advantageously by gel permeation chromatography (GPC) in 1.5% by weight aqueous formic acid as eluent and cross-linked poly-hydroxyethylmethacrylate as stationary phase. In other embodiments, polyethoxylated polypropylenimines are preferred, with an average molecular weight $M_w$ in a range of from 2,500 to 50,000 g/mol, determined advantageously by gel permeation chromatography (GPC) in 1.5% by weight aqueous formic acid as eluent and cross-linked poly-hydroxyethylmethacrylate as stationary phase.

Polyethylenimines and polypropylenimines, non-substituted or substituted as above, may applied in small amounts, for example 0.01 to 2% by weight, referring to the total solids content of the respective inventive automatic dishwashing formulation.

The cleaning composition of the presently claimed invention may comprise more than one additive. For example, the cleaning composition of the present invention may comprise as additive, a surfactant, a builder and a combination of the foregoing.

In one embodiment of the present invention, the cleaning composition of the present invention are free from heavy metals apart from zinc compounds. Within the context of the present, this may be understood as meaning that the cleaning compositions are free from those heavy metal compounds which do not act as bleach catalysts, in particular of compounds of iron and of bismuth. Within the context of the present invention, "free from" in connection with heavy metal compounds is to be understood as meaning that the content of heavy metal compounds that do not act as bleach catalysts is in sum in the range from 0 to 100 ppm, determined by the leach method and based on the solids content. Preferably, detergent compositions according to the invention has, apart from zinc, a heavy metal content below 0.05 ppm, based on the solids content of the formulation in question. The fraction of zinc is thus not included.

Within the context of the present invention, "heavy metals" are defined to be any metal with a specific density of at least 6 $g/cm^3$ with the exception of zinc. In particular, the heavy metals are metals such as bismuth, iron, copper, lead, tin, nickel, cadmium and chromium.

Preferably, inventive automatic dishwashing formulations comprise no measurable fractions of bismuth compounds, i.e. for example less than 1 ppm.

In one embodiment of the present invention, inventive compositions comprise, in addition to additives, one or more further ingredient such as organic solvents, buffers, disintegrants for tabs, and/or acids such as methylsulfonic acid.

Advantages

The present invention offers one or more of the following advantages:

1. Good spotting results are obtained at lower dosage levels.
2. The compounds of the present invention have high compatibility with silver, ceramics and plastic.
3. Compounds of the present invention are compatible with a wide variety of dishwashing additives.
4. Good rinse result is obtained at reduced temperature program using the dishwashing composition comprising the compounds of the present invention.
5. The compounds of the presently claimed invention have beneficial ecotoxicity profile such as anaerobic biodegradability.

EMBODIMENTS

1. A compound of general formula (I)

$$R^1—CHR^2—CH_2—O\text{-}(AO)_x—CH_2—CH(OH)—R^3 \quad (I)$$

wherein $R^1$ is linear or branched, unsubstituted $C_2$-$C_4$-alkyl, $R^2$ is linear or branched, unsubstituted alkyl group bearing two carbon atoms more than $R^1$, x is an integer in the range of from 10 to 35, AO is identical or different and selected from $CH_2$—$CH_2$—O, $(CH_2)_3$—O, $(CH_2)_4$—O, $CH_2CH(CH_3)$—O, $CH(CH_3)$—$CH_2$—O— and $CH_2CH(n\text{-}C_3H_7)$—O, and $R^3$ is linear or branched, unsubstituted or substituted $C_6$-$C_{18}$-alkyl.

2. The compound according to embodiment 1, wherein $R^1$ is selected from the group consisting of ethyl, n-propyl and iso-propyl.
3. The compound according to embodiment 1, wherein $R^2$ is selected from the group consisting of n-butyl, iso-butyl, n-pentyl, iso-pentyl, 3-methylpentyl, n-hexyl, iso-hexyl and mixtures thereof.
4. The compound according to embodiment 1, wherein $R^3$ is selected from the group consisting of n-hexyl, n-octyl, n-decyl, n-dodecyl and mixtures thereof.
5. The compound according to one or more of embodiments 1 to 4, wherein $R^1$ is propyl and $R^2$ is selected from the group consisting of n-pentyl, iso-pentyl and mixtures thereof.
6. The compound according to one or more of embodiments 1 to 5, wherein AO is identical and is $CH_2$—$CH_2$—O.
7. The compound according to embodiment 1, wherein AO is $(PO)_y$-$(EO)_{x-y}$ and y is in the range of from 0.2 to 2.
8. The compound according to one or more of embodiments 1 to 5 or 7 wherein AO is PO-$(EO)_{x-1}$.
9. A process for preparing compound of general formula (I) as defined in one or more of embodiments 1 to 8, comprising the steps of
   (a) reacting an alcohol of the formula $R^1$—$CHR^2$—$CH_2$—OH with one or more $C_2$-$C_4$-alkylene oxides,
   (b) reacting the reaction mixture obtained in step (a) with an epoxide according to formula (II)

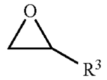

(II)

wherein $R^3$ is linear or branched, unsubstituted or substituted $C_6$-$C_{18}$-alkyl.
10. The process according to embodiment 9, wherein in step (a) the temperature is in the range of 70° C. to 250° C.
11. The process according to embodiment 9 or 10, wherein the reaction time of step (a) is in the range of 0.5 hour to 12 hours.
12. The process according to embodiment 9, wherein in step (b) the temperature is in the range of 120° C. to 200° C.
13. The process according to embodiment 9 or 12, wherein the reaction time of step (b) is in the range of from 1 hour to 6 hours.
14. The process according to one or more of embodiments 9 to 13, further comprising at least one solvent.
15. The process according to embodiment 14, wherein the at least one solvent is selected from the group consisting of hexane, cyclohexane, toluene and xylene, tetrahydrofuran, 1,4-dioxane, dimethylformamide, dimethylacetamide and N-methylpyrrolidone.
16. The process according to one or more of embodiments 9 to 15 wherein steps (a) and (b) are carried out in bulk.
17. Use of a compound according to any of embodiments 1 to 8 or of a combination of at least two compounds according to any of embodiments 1 to 8 in a cleaning composition for automatic dishwashing.
18. A process for cleaning dishware in an automatic dishwasher by using a composition that contains at least one compound of formula (I) according to one or more of embodiments 1 to 8.
19. A cleaning composition comprising
   (A) at least one compound of general formula (I) according to one or more of embodiments 1 to 8, and
   (B) at least one additive.
20. The cleaning composition according to embodiment 19 comprising
   (A) 0.5 to 10% by weight of at least one compound of general formula (I) according to one or more of embodiments 1 to 8, and
   (B) 1 to 50% by weight of at least one additive;
   by weight of the final weight of the cleaning composition.
21. The cleaning composition according to embodiment 19 or 20, wherein the at least one additive is selected from the group consisting of chelating agents, enzymes, builders, cobuilders, alkali metal carriers, bleaching agents, bleach catalysts, bleach activators, dyes, perfumes, corrosion inhibitors, anti-redeposition agents and fillers.

EXAMPLES

Compounds

Compound of general formula (I), (A.1):

$n$-$C_5H_{11}$—$CH(n\text{-}C_3H_7)$—$CH_2$—O-$(EO)_{21}$—$CH_2$—CH(OH)-$n$-$C_{10}H_{21}$ (1)

$n$-$C_5H_{11}$—$CH(n\text{-}C_3H_7)$—$CH_2$—O-$(EO)_{23}$—$CH_2$—CH(OH)-$n$-$C_{10}H_{21}$ (II)

Compounds used in Comparative examples, (B.1):

iso-$C_{11}H_{23}$—O-$(EO)_{21}$—$CH_2$—CH(OH)-$n$-$C_{10}H_{21}$ (III)

iso-$C_9H_{19}$—O-$(EO)_{20}$—$CH_2$—CH(OH)-$n$-$C_{10}H_{21}$ (IV)

iso-$C_{13}H_{27}$—O-$(EO)_{26}$—$CH_2$—CH(OH)-$n$-$C_{10}H_{21}$ (V)

iso-$C_{11}H_{23}$—O-$(EO)_{22}$—$CH_2$—CH(OH)-$n$-$C_8H_{17}$ (VI)

Additives

Chelating agent 1: Trisodium salt of methyl glycinediacetic acid (MGDA-$Na_3$)

Chelating agent 2: Trisodium citrate dihydrate

Enzyme 1: Protease

Enzyme 2: Amylase

Builder 1: Polyacrylic acid $M_w$ 4000 g/mol as sodium salt, completely neutralized.

Builder 2: Polycarboxylate polymer of 2-Acrylamido-2-methylpropane sulfonic acid and acrylic acid Builder 3: $Na_2Si_2O_5$ Cobuilder: 1-hydroxyethane-1,1-diphosphonate (HEDP)

Bleaching agent: Sodium percarbonate

Filler: Sodium sulfate

Bleach activator: tetraacetylethylenediamine (TAED)

Alkali metal carrier: $Na_2CO_3$

The cleaning composition for automatic dishwashing are prepared according to table 1.

TABLE 1

| All amounts in g/ sample | ADW.1 | ADW.2 | ADW.3 | ADW.4 | ADW.5 | ADW.6 | ADW.7 |
|---|---|---|---|---|---|---|---|
| Chelating agent 1 | 40.0 | 10.0 | 0.0 | 0.0 | 25.0 | 35.0 | 40.0 |
| Enzyme 1 | 2.5 | 2.5 | 2.5 | 2.5 | 2.5 | 2.5 | 2.5 |
| Enzyme 2 | 1.0 | 1.0 | 1.0 | 1.0 | 1.0 | 1.0 | 1.0 |
| Compound according to general formula (I), (A.1) | 3.0 to 5.0 | 3.0 to 5.0 | 3.0 to 5.0 | 3.0 to 5.0 | 3.0 to 5.0 | 3.0 to 5.0 | 3.0 to 5.0 |
| Builder 1 | 5.0 | 5.0 | 0.0 | 0.0 | 0.0 | 0.0 | 0.0 |
| Builder 2 | 0.0 | 0.0 | 5.0 | 5.0 | 5.0 | 5.0 | 5.0 |
| Bleaching agent | 15.0 | 10.2 | 10.2 | 10.2 | 10.2 | 10.2 | 15.0 |
| Filler | 1.0 | 0.0 | 0.0 | 9.5 | 9.5 | 0.0 | 1.0 |
| Bleach activator | 4.0 | 4.0 | 4.0 | 4.0 | 4.0 | 4.0 | 4.0 |
| Builder 3 | 2.0 | 2.0 | 2.0 | 2.0 | 2.0 | 2.0 | 2.0 |
| Alkali metal carrier | 23.7 | 24.5 | 34.5 | 35.0 | 35.0 | 34.5 | 23.7 |
| Chelating agent 2 | 0.0 | 35.0 | 30.0 | 25.0 | 0.0 | 0.0 | 0.0 |
| Cobuilder | 0.8 | 0.8 | 5.8 | 0.8 | 0.8 | 0.8 | 0.8 |

Cleaning compositions prepared according to Table-1 are excellent in rinsing, especially when used as automatic dishwashing compositions.

Example I

Rinse Performance

Rinsing Experiments:

The rinsing experiments of example I were carried out in Miele automatic dish wash machines, type G1223 GSL2. The program 50° C. ("R-time 2", for washing) and 65° for rinsing was selected.

No separate rinsing agent was added, no regenerating salt was used. The dishwash experiments were carried out with water, 21° dH (German hardness), (Ca:Mg):$HCO_3$ (3:1): 1.35. In each experiment eight tea cups and nine dinner plates were placed in the dishwasher as base load. For evaluation in each experiment three knives (stainless steel), three blue melamine resin plates, three drinking glasses and three plates from china were placed in the dishwasher. Before each cycle 100 g of soil, comprising fat, protein and starch in the form of margarine, egg-yolk and starch, were added. In each cycle, 18 g of the detergent compositions for automatic dishwashing ADW.3 according to table 1 were added into the dosing chamber of the machine.

Between two cycles, a waiting period of one hour was hold, of which 10 minutes were with the door of the dishwashing machine closed and 50 minutes with open door. The dishes for the evaluation were checked by visual assessment of the ware after 6 cycles in a darkened chamber under light behind an aperture diaphragm was awarded using a grading scale from 1 (very poor) to 10 (very good). The grades for each type of table ware (knives (stainless steel), blue melamine resin plates, drinking glasses, plates from china) were summed up and divided by the number (3) of tableware. Results are found in table 2. Σ Spotting is the sum of the values for all 4 different tableware types. The standard deviation of the grades in the comparative test is ±0.5.

The 18 g portions of the detergent compositions for automatic dishwashing ADW.3 according to table 1 were made by mixing the solid ingredients except (A.1) and weighing portions of 17.1 g of this base mixture. To each portion the associated quantity found in table 2 of molten (A.1) in case of inventive examples and molten (B.1) in case of comparative examples was added and distributed (A.1) or (B.1) homogeneously in the mixture before adding into the dosing chamber of the dishwashing machine.

TABLE 2

| Rinsing Test | | | | | | | | | |
|---|---|---|---|---|---|---|---|---|---|
| Example no. | Formulation (ADW.3) | base mixture [g] | (A.1) [g] | (B.1) [g] | Spotting, knives (scale) | Spotting, glass (scale) | Spotting melamine (scale) | Spotting, china (scale) | Σ Spotting |
| Comparative ex. 1 | (B.1) (III) | 17.10 | | 0.90 | 10.0 | 3.7 | 2.7 | 7.3 | 23.7 |
| Comparative ex. 2 | (B.1) (III) | 17.10 | | 0.54 | 1.0 | 1.0 | 1.7 | 1.0 | 4.7 |
| Inventive example 1 | (A.1) (II) | 17.10 | 0.90 | | 10.0 | 8.7 | 5.7 | 8.7 | 33.1 |
| Inventive example 2 | (A.1) (II) | 17.10 | 0.54 | | 8.7 | 3.0 | 2.0 | 3.3 | 17.0 |
| Comparative ex. 3 | (B.1) (IV) | 17.10 | | 0.90 | 9.0 | 4.3 | 4.3 | 6.0 | 23.6 |
| Comparative ex. 4 | (B.1) (IV) | 17.10 | | 0.54 | 5.0 | 2.0 | 1.3 | 2.0 | 10.3 |
| Comparative ex. 5 | (B.1) (V) | 17.10 | | 0.90 | 10.0 | 4.7 | 1.7 | 6.7 | 23.1 |
| Comparative ex. 6 | (B.1) (V) | 17.10 | | 0.54 | 10.0 | 2.0 | 1.3 | 2.7 | 16.0 |

As is evident from Table 2, the spotting results for knives, glass, melanin and china were higher when the cleaning composition comprised the inventive compounds of general formula (I) compared to the comparative examples. The compounds of the present invention provide a better spotting effect on different materials varying from steel, glass, plastic and china.

Example II

Rinsing Experiments:

The rinsing experiments of example 11 were carried out in Miele automatic dish wash machines, type G1223 GSL2. The program 50° C. ("R-time 2", for washing) and 65' for rinsing was selected. No separate rinsing agent was added, no regenerating salt was used. The dish-wash experiments were carried out with water, 21° dH (German hardness), (Ca:Mg):$HCO_3$ (3:1):1.35. In each experiment eight tea cups and nine dinner plates were placed in the dishwasher as base load. For evaluation in each experiment three knives (stainless steel), three blue melamine resin plates, three drinking glasses and three plates from china were placed in the dishwasher. Before each cycle 100 g of soil, comprising fat, protein and starch in the form of margarine, egg-yolk and starch, were added. In each cycle, 18 g of the detergent compositions for automatic dishwashing ADW.2 according to table 1 were added into the dosing chamber of the machine.

Between two cycles, a waiting period of one hour was hold, of which 10 minutes were with the door of the dishwashing machine closed and 50 minutes with open door. The dishes for the evaluation were checked by visual assessment of the ware after 6 cycles in a darkened chamber under light behind an aperture diaphragm was awarded using a grading scale from 1 (very poor) to 10 (very good). The grades for each type of table ware (knives (stainless steel), blue melamine resin plates, drinking glasses, plates from china) were summed up and divided by the number (3) of tableware. Results are found in table 3. Σ Spotting is the sum of the values for all 4 different tableware types. The standard deviation of the grades in the comparative test is ±0.5.

The 18 g portions of the detergent compositions for automatic dishwashing ADW.2 according to table 1 were made by mixing the solid ingredients except (A.1) and weighing portions of 17.1 g of this base mixture. To each portion the associated quantity found in table 3 of molten (A.1) in case of inventive examples and molten (B.1) in case of comparative examples was added and distributed (A.1) or (B.1) homogeneously in the mixture before adding into the dosing chamber of the dishwashing machine.

TABLE 3

Rinsing Test

| Example | Formulation (ADW.2) | base mixture [g] | (A.1) [g] | (B.1) [g] | Spotting, knives | Spotting, glass | Spotting melamine | Spotting, china | Σ Spotting |
|---|---|---|---|---|---|---|---|---|---|
| Comparative ex. 7 | (B.1) (III) | 17.10 | | 0.90 | 10.0 | 5.7 | 4.0 | 8.3 | 28.0 |
| Comparative ex. 8 | (B.1) (III) | 17.10 | | 0.54 | 2.3 | 2.0 | 3.3 | 2.3 | 9.9 |
| Inventive example 3 | (A.1) (II) | 17.10 | 0.90 | | 10.0 | 7.0 | 8.0 | 10.0 | 35.0 |
| Inventive example 4 | (A.1) (II) | 17.10 | 0.54 | | 10.0 | 8.0 | 4.3 | 9.7 | 32.0 |
| Comparative ex. 9 | (B.1) (IV) | 17.10 | | 0.90 | 10.0 | 9.0 | 5.7 | 10.0 | 34.7 |
| Comparative ex. 10 | (B.1) (IV) | 17.10 | | 0.54 | 8.7 | 5.3 | 5.0 | 5.0 | 24.0 |
| Comparative ex. 11 | (B.1) (V) | 17.10 | | 0.90 | 10.0 | 9.0 | 4.0 | 10.0 | 33.0 |
| Comparative ex. 12 | (B.1) (V) | 17.10 | | 0.54 | 7.0 | 2.0 | 3.3 | 4.7 | 17.0 |

The composition comprising the compound of the presently claimed invention exhibit an improved spotting as shown by the higher value on the grading scale for all the types of material compared to the comparative compositions.

Example III

Rinsing Experiments:

The rinsing experiments of example Ill were carried out in Miele automatic dishwash machines, type G1223 GSL2. The program 45° C. ("R-time 2", for washing) and 550 for rinsing was selected. No separate rinsing agent was added, no regenerating salt was used. The dishwash experiments were carried out with water, 21° dH (German hardness), (Ca:Mg):$HCO_3$ (3:1):1.35. In each experiment eight tea cups and nine dinner plates were placed in the dishwasher as base load. For evaluation in each experiment three knives (stainless steel), three blue melamine resin plates, three drinking glasses and three plates from china were placed in the dishwasher. Before each cycle 100 g of soil, comprising fat, protein and starch in the form of margarine, egg-yolk and starch, were added. In each cycle, 18 g of the detergent compositions for automatic dishwashing ADW.1 and ADW.7 according to table 1 were added into the dosing chamber of the machine.

Between two cycles, a waiting period of one hour was hold, of which 10 minutes were with the door of the dishwashing machine closed and 50 minutes with open door. The dishes for the evaluation were checked by visual assessment of the ware after 6 cycles in a darkened chamber under light behind an aperture diaphragm was awarded using a grading scale from 1 (very poor) to 10 (very good). The grades for each type of table ware (knives (stainless steel), blue melamine resin plates, drinking glasses, plates from china) were summed up and divided by the number (3) of tableware. Results are found in table 4. Σ Spotting is the sum of the values for all 4 different tableware types. The standard deviation of the grades in the comparative test is ±0.5.

The 18 g portions of the detergent compositions for automatic dishwashing ADW.1 and ADW.7 according to table 1 were made by mixing the solid ingredients except (A.1) and weighing portions of 17.1 g of this base mixture. To each portion the associated quantity found in table 4 of molten (A.1) in case of inventive examples and molten (B.1) in case of comparative examples was added and distributed (A.1) or (B.1) homogeneously in the mixture before adding into the dosing chamber of the dishwashing machine.

TABLE 4

Rinsing Test

| Example no. | Formulation (ADW.1) | base mixture [g] | (A.1) [g] | (B.1) [g] | Spotting, knives | Spotting, glass | Spotting melamine | Spotting, china | Σ Spotting |
|---|---|---|---|---|---|---|---|---|---|
| Comparative ex. 13 | (B.1) (I) | 17.10 | | 0.63 | 10.0 | 8.0 | 2.7 | 7.3 | 28.0 |
| Inventive example 5 | (A.1) (II) | 17.10 | 0.63 | | 10.0 | 8.0 | 3.3 | 9.0 | 30.3 |
| | **Formulation (ADW.7)** | **base mixture [g]** | **(A.1) [g]** | **(A.1) [g]** | **Spotting, knives** | **Spotting, glass** | **Spotting melamine** | **Spotting, china** | **Σ Spotting** |
| Comparative ex. 14 | (B.1) (III) | 17.10 | | 0.63 | 2.3 | 4.3 | 3.0 | 4.3 | 13.9 |
| Inventive example 6 | (A.1) (II) | 17.10 | 0.63 | | 10.0 | 7.7 | 3.7 | 8.7 | 30.1 |

Example IV

Rinsing Experiments:

The rinsing experiments of example IV were carried out in Miele automatic dishwash machines, type G1223 GSL2. The program 50° C. (“R-time 2”, for washing) and 65° for rinsing was selected. No separate rinsing agent was added, no regenerating salt was used. The dishwash experiments were carried out with water, 21° dH (German hardness), (Ca:Mg):$HCO_3$ (3:1):1.35. In each experiment eight tea cups and nine dinner plates were placed in the dishwasher as base load. For evaluation in each experiment three knives (stainless steel), three blue melamine resin plates, three drinking glasses and three plates from china were placed in the dishwasher. Before each cycle 100 g of soil, comprising fat, protein and starch in the form of margarine, egg-yolk and starch, were added. In each cycle, 18 g of the detergent compositions for automatic dishwashing ADW.4, ADW.5 and ADW.6 according to table 1 were added into the dosing chamber of the machine.

Between two cycles, a waiting period of one hour was hold, of which 10 minutes were with the door of the dishwashing machine closed and 50 minutes with open door. The dishes for the evaluation were checked by visual assessment of the ware after 6 cycles in a darkened chamber under light behind an aperture diaphragm was awarded using a grading scale from 1 (very poor) to 10 (very good). The grades for each type of table ware (knives (stainless steel), blue melamine resin plates, drinking glasses, plates from china) were summed up and divided by the number (3) of tableware. Results are found in table 5. Σ Spotting is the sum of the values for all 4 different tableware types. The standard deviation of the grades in the comparative test is ±0.5.

The 18 g portions of the detergent compositions for automatic dishwashing ADW.4, ADW.5 and ADW.6 according to table 1 were made by mixing the solid ingredients except (A.1) and weighing portions of 17.1 g of this base mixture. To each portion the associated quantity found in table 5 of molten (A.1) in case of inventive examples and molten (B.1) in case of comparative examples was added and distributed (A.1) or (B.1) homogeneously in the mixture before adding into the dosing chamber of the dishwashing machine.

TABLE 5

Rinsing Test

| Example no. | Formulation (ADW.4) | base mixture [g] | (A.1) [g] | (B.1) [g] | Spotting, knives | Spotting, glass | Spotting melamine | Spotting, china | Σ Spotting |
|---|---|---|---|---|---|---|---|---|---|
| Comparative ex. 15 | (B.1) (III) | 17.10 | | 0.72 | 10.0 | 3.7 | 2.7 | 3.7 | 20.1 |
| Inventive example 7 | (A.1) (II) | 17.10 | 0.72 | | 10.0 | 4.3 | 8.7 | 7.3 | 30.3 |
| | Formulation (ADW.5) | base mixture [g] | (A.1) [g] | (B.1) [g] | Spotting, knives | Spotting, glass | Spotting melamine | Spotting, china | Σ Spotting |
| Comparative ex. 16 | (B.1) (III) | 17.10 | | 0.72 | 10.0 | 2.7 | 4.3 | 3.7 | 20.7 |
| Inventive example 8 | (A.1) (II) | 17.10 | 0.72 | | 10.0 | 6.7 | 6.0 | 7.0 | 29.7 |
| | Formulation (ADW.6) | base mixture [g] | (A.1) [g] | (B.1) [g] | Spotting, knives | Spotting, glass | Spotting melamine | Spotting, china | Σ Spotting |
| Comparative ex. 17 | (B.1) (III) | 17.10 | | 0.72 | 8.0 | 6.0 | 3.7 | 5.0 | 22.7 |
| Inventive example 9 | (A.1) (II) | 17.10 | 0.72 | | 10.0 | 5.3 | 6.0 | 10.0 | 31.3 |

Example V

Drying Experiments

The drying experiments of example V were carried out in Miele automatic dishwash machines, type G1223 GSL2. The program 45° C. ("R-time 2", for washing) and 550 for rinsing was selected. No separate rinsing agent was added, no regenerating salt was used. The dishwash experiments were carried out with water, 21° dH (German hardness), (Ca:Mg):$HCO_3$ (3:1):1.35.

A full load of tableware with items of different material were used (metal, glass, porcelain, plastic). For each cycle the detergent according to table 6 and 50 g of ballast soil were added to the machine. The first three cycles are used to condition the dishwasher. After these 3 conditioning cycles the next three cycles were evaluated. For the evaluation cycles, the machine is opened 30 minutes after end of machine program and residual water drops on all items are counted within about 10 minutes. Number of drops are counted from best 0=no water drops to 8=8 or more water drops left. Average value for each tableware group is calculated per cycle and average values of three evaluation cycles are calculated. In addition a average of all tableware groups is calculated. The standard deviation of the average values in the comparative test is ±0.5.

Machine Load:

- 11 Dinner plates (tableware group porcelain)
- 3 blue SAN plates (tableware group plastics)
- 3 red PP plates (tableware group plastics)
- 8 Soup plates (tableware group porcelain)
- 7 dessert plates (tableware group porcelain)
- 6 Tupperware boxes (tableware group plastics)
- 6 beakers (tableware group gasses)
- 10 cups (tableware group porcelain)
- 6 drinking glasses (tableware group gasses)
- 12 knives (tableware group cutlery)
- 6 forks (tableware group cutlery)
- 6 soup spoons (tableware group cutlery)
- 6 desert forks (tableware group cutlery)
- 6 coffee spoons (tableware group cutlery)

TABLE 6

Drying Test

| Example no. | Formulation (ADW.2) | base mixture [g] | (A.1) [g] | (B.1) [g] | Average of droplets on porcelain | Average of droplets on plastics | Average of droplets on glasses | Average of droplets on cutlery | Average of droplets on all tableware groups |
|---|---|---|---|---|---|---|---|---|---|
| Comparative ex. 18 | (B.1) (I) | 17.10 | | 0.54 | 3.40 | 7.28 | 2.39 | 0.98 | 3.51 |
| Inventive example 10 | (A.1) (I) | 17.10 | 0.54 | | 3.21 | 4.33 | 1.33 | 0.70 | 2.40 |
| Comparative ex. 19 | (B.1) (III) | 17.10 | | 0.72 | 2.95 | 3.44 | 1.14 | 0.50 | 2.01 |

TABLE 6-continued

| Drying Test | | | | | | | | | |
|---|---|---|---|---|---|---|---|---|---|
| Example no. | Formulation (ADW.2) | base mixture [g] | (A.1) [g] | (B.1) [g] | Average of droplets on porcelain | Average of droplets on plastics | Average of droplets on glasses | Average of droplets on cutlery | Average of droplets on all table-ware groups |
| Inventive example 11 | (A.1) (I) | 17.10 | 0.72 | | 2.37 | 2.72 | 0.78 | 0.44 | 1.58 |
| Comparative ex. 20 | (B.1) (III) | 17.10 | | 0.90 | 2.30 | 2.97 | 0.97 | 0.29 | 1.38 |
| Inventive example 12 | (A.1) (I) | 17.10 | 0.90 | | 1.77 | 0.75 | 0.78 | 0.00 | 0.79 |

Example VI

Fat Residue

The determination of fat residues of example VI was carried out in Miele automatic dish wash machines, type G 1223 SC GSL2. The program 45° C. ("R-time 2", for washing) and 55° for rinsing was selected. No separate rinsing agent was added, no regenerating salt was used. The dish-wash experiments were carried out with water, 21° dH (German hardness), (Ca:Mg):$HCO_3$ (3:1):1.35.

In each experiment three stainless steel knives eight tea cups and nine dinner plates were placed in the dishwasher as base load. Before each cycle, 5 g of Biskin Gold®, a solid vegetable fat, and 5 g of margarine were added into the machine. For each cycle the detergent formulation according to table 7 were added to the machine, consisting of base mixture and (A.1) in case of inventive examples and molten (B.1) in case of comparative examples. 5 cycles were run without drying times between cycles. After the $5^{th}$ cycles the filters from the bottom of the machines were taken out of the machine and dried for 18 h at ambient conditions. The weights of the filters were determined and the differences to their weights before the first cycle were calculated (fat residue [g]=weight of filter before test [g]−weight of filter after test). The standard deviation of the fat residue is ±0.2 g.

The results are summarized in table 7.

TABLE 7

| Fat residue test | | | | | |
|---|---|---|---|---|---|
| Example no. | Formulation (ADW.2) | base mixture [g] | (A.1) [g] | B.1 | Fat residue [g] |
| Comparative ex. 21 | (B.1) (VI) | 17.10 | — | 0.54 | 3.37 |
| Comparative ex. 22 | (B.1) (VI) | 17.10 | — | 0.72 | 5.12 |
| Inventive example 13 | (A.1) (I) | 17.10 | 0.54 | — | 2.48 |
| Inventive example 14 | (A.1) (I) | 17.10 | 0.72 | — | 3.27 |

As seen in Table 7, the amount of fat residue in case of formulations containing the compounds of the inventive examples is less compared to the comparative examples.

The invention claimed is:

1. A compound of general formula (I)

$$R^1—CHR^2—CH_2—O\text{-}(AO)_x—CH_2—CH(OH)—R^3 \quad (I)$$

wherein $R^1$ is linear or branched, unsubstituted $C_2$-$C_4$-alkyl, $R^2$ is linear or branched, unsubstituted alkyl group bearing two carbon atoms more than $R^1$, x is an integer in a range of from 10 to 30, AO is identical or different and selected from the group consisting of $CH_2—CH_2—O$, $(CH_2)_3—O$, $(CH_2)_4—O$, $CH_2CH(CH_3)—O$, $CH(CH_3)—CH_2—O—$ and $CH_2CH(n\text{-}C_3H_7)—O$, and $R^3$ is linear or branched, unsubstituted or substituted $C_6$-$C_{18}$-alkyl.

2. The compound according to claim 1, wherein x is an integer in a range of from 21 to 30.

3. The compound according to claim 1, wherein $R^3$ is selected from the group consisting of n-hexyl, n-octyl, n-decyl, n-dodecyl and mixtures thereof.

4. The compound according to claim 1, wherein AO is identical and is $CH_2—CH_2—O$.

5. The compound according to claim 1, wherein AO is $(PO)_y$-$(EO)_{x-y}$, and y is in a range of from 0.2 to 2.

6. The compound according to claim 1, wherein AO is PO-$(EO)_{x-1}$.

7. A process for preparing the compound of general formula (I) according to claim 1 comprising the steps of (a) reacting an alcohol of the formula $R^1—CHR^2—CH_2—OH$ with one or more $C_2$-$C_4$-alkylene oxides, (b) reacting the reaction mixture obtained in step (a) with an epoxide according to formula (II)

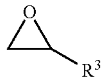

(II)

wherein $R^3$ is linear or branched, unsubstituted or substituted $C_6$-$C_{18}$-alkyl.

8. The process according to claim 7 wherein steps (a) and (b) are carried out in bulk.

9. A cleaning composition for automatic dishwashing comprising the compound according to claim 1.

10. A cleaning composition comprising (A) at least one compound of general formula (I) according to claim 1, and (B) at least one additive.

11. The cleaning composition according to claim 10 comprising (A) 0.5 to 10% by weight of the at least one compound of general formula (I), and (B) 1 to 50% by weight of the at least one additive;

by weight of a final weight of the cleaning composition.

12. The cleaning composition according to claim 10, wherein the at least one additive is selected from the group consisting of chelating agents, enzymes, builders, cobuilders, alkali metal carriers, bleaching agents, bleach catalysts, bleach activators, dyes, perfumes, corrosion inhibitors, anti-redeposition agents and fillers.

13. The cleaning composition according to claim 11, wherein the at least one additive is selected from the group consisting of chelating agents, enzymes, builders, cobuilders, alkali metal carriers, bleaching agents, bleach catalysts, bleach activators, dyes, perfumes, corrosion inhibitors, anti-redeposition agents and fillers.

14. A cleaning composition for automatic dishwashing comprising a combination of at least two compounds according to claim 1.

* * * * *